US011565047B2

(12) United States Patent
Liu et al.

(10) Patent No.: US 11,565,047 B2
(45) Date of Patent: Jan. 31, 2023

(54) WEARABLE NON-LIQUID MEDICATION INJECTION DEVICE

(71) Applicant: Verily Life Sciences LLC, South San Francisco, CA (US)

(72) Inventors: Zenghe Liu, Alameda, CA (US); Todd Whitehurst, Redwood City, CA (US); Michael Chen, Sunnyvale, CA (US); Clarissa Lui, Menlo Park, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 298 days.

(21) Appl. No.: 15/865,564

(22) Filed: Jan. 9, 2018

(65) Prior Publication Data

US 2021/0060252 A1    Mar. 4, 2021

Related U.S. Application Data

(60) Provisional application No. 62/505,457, filed on May 12, 2017, provisional application No. 62/444,237, filed on Jan. 9, 2017.

(51) Int. Cl.
*A61M 5/20* (2006.01)
*A61M 5/32* (2006.01)
(Continued)

(52) U.S. Cl.
CPC ...... *A61M 5/2046* (2013.01); *A61M 5/14248* (2013.01); *A61M 5/155* (2013.01);
(Continued)

(58) Field of Classification Search
CPC ...... A61M 5/145; A61M 5/158; A61M 5/155; A61M 5/172; A61M 2005/2026;
(Continued)

(56) References Cited

U.S. PATENT DOCUMENTS

| 3,845,318 A | 10/1974 | Thillays |
| 4,031,889 A * | 6/1977 | Pike .................. A61M 5/24 |
| | | 604/144 |

(Continued)

FOREIGN PATENT DOCUMENTS

| EP | 2058020 | 5/2009 |
| WO | 8601120 | 2/1986 |

(Continued)

OTHER PUBLICATIONS

International Application No. PCT/US2018/012940, "International Search Report and Written Opinion", dated May 8, 2018, 16 pages.

(Continued)

*Primary Examiner* — Bhisma Mehta
*Assistant Examiner* — William R Frehe
(74) *Attorney, Agent, or Firm* — Kilpatrick Townsend & Stockton LLP (57) ABSTRACT

The present disclosure relates to relates to medication injection devices, and in particular to systems and methods for on-demand delivery of a non-liquid medication from a wearable medication injection device. Particularly, aspects of the present invention are directed to a device that includes a housing defining a chamber, a piston disposed within the chamber, a needle disposed within the chamber on a first side of the piston, an energetic material disposed within the chamber on a second side of the piston, and a medication strip disposed within the needle. The medication strip includes an injectable substance in a non-liquid form.

11 Claims, 7 Drawing Sheets

(51) Int. Cl.
*A61M 5/172* (2006.01)
*A61M 5/315* (2006.01)
*A61M 5/19* (2006.01)
*A61M 5/158* (2006.01)
*A61M 5/24* (2006.01)
*A61M 5/142* (2006.01)
*A61M 5/155* (2006.01)
*A61M 37/00* (2006.01)
*A61K 9/00* (2006.01)

(52) U.S. Cl.
CPC .......... *A61M 5/158* (2013.01); *A61M 5/1723* (2013.01); *A61M 5/19* (2013.01); *A61M 5/2033* (2013.01); *A61M 5/2066* (2013.01); *A61M 5/24* (2013.01); *A61M 5/3153* (2013.01); *A61M 5/3234* (2013.01); *A61M 5/3286* (2013.01); *A61M 5/3287* (2013.01); *A61M 5/3293* (2013.01); *A61M 37/0069* (2013.01); *A61K 9/0024* (2013.01); *A61M 5/3202* (2013.01); *A61M 2005/14256* (2013.01); *A61M 2005/1581* (2013.01); *A61M 2005/1585* (2013.01); *A61M 2005/206* (2013.01); *A61M 2005/2026* (2013.01); *A61M 2005/2086* (2013.01); *A61M 2205/0266* (2013.01); *A61M 2205/123* (2013.01); *A61M 2205/3303* (2013.01); *A61M 2205/3569* (2013.01); *A61M 2205/3584* (2013.01); *A61M 2205/3592* (2013.01); *A61M 2205/36* (2013.01); *A61M 2205/8206* (2013.01); *A61M 2209/088* (2013.01); *A61M 2230/201* (2013.01)

(58) Field of Classification Search
CPC ...... A61M 2005/14204; A61M 5/2046; A61M 2205/8218; A61M 2205/8225; A61M 2205/8231; A61M 37/0069
See application file for complete search history.

(56) References Cited

U.S. PATENT DOCUMENTS

| | | | |
|---|---|---|---|
| 4,307,298 | A | 12/1981 | El Hamamsy et al. |
| 4,430,739 | A | 2/1984 | McMahan |
| 4,994,028 | A * | 2/1991 | Leonard ............ A61M 37/0069 604/59 |
| 5,131,377 | A | 7/1992 | Taruya et al. |
| 5,290,228 | A | 3/1994 | Uemura et al. |
| 5,476,449 | A | 12/1995 | Richmond |
| 5,599,312 | A | 2/1997 | Higashikawa |
| 5,637,087 | A | 6/1997 | O'Neil et al. |
| 5,785,688 | A | 7/1998 | Joshi et al. |
| 5,851,197 | A | 12/1998 | Marano et al. |
| 5,860,957 | A | 1/1999 | Jacobsen et al. |
| 6,045,534 | A | 4/2000 | Jacobsen et al. |
| 6,335,538 | B1 | 1/2002 | Prutchi et al. |
| 6,422,145 | B1 | 7/2002 | Gavrilovic et al. |
| 6,729,240 | B1 | 5/2004 | Smith et al. |
| 7,699,804 | B2 | 4/2010 | Barry et al. |
| 8,353,877 | B2 | 1/2013 | Hallahan et al. |
| 8,900,194 | B2 | 12/2014 | Ferber et al. |
| 9,289,123 | B2 | 3/2016 | Weibel et al. |
| 9,717,859 | B2 | 8/2017 | Harms et al. |
| 10,598,583 | B1 | 3/2020 | Peeters et al. |
| 2001/0050618 | A1 | 12/2001 | Dummermuth et al. |
| 2002/0052579 | A1 | 5/2002 | Sogaro |
| 2002/0068907 | A1 | 6/2002 | Dysarz |
| 2003/0114789 | A1 | 6/2003 | Haar et al. |
| 2003/0187396 | A1 | 10/2003 | Ponzi |
| 2004/0082908 | A1 | 4/2004 | Whitehurst et al. |
| 2008/0203112 | A1 | 8/2008 | Peuker et al. |
| 2008/0262431 | A1 | 10/2008 | Anderson et al. |
| 2008/0287883 | A1 | 11/2008 | Radmer et al. |
| 2008/0306436 | A1 | 12/2008 | Edwards et al. |
| 2009/0093793 | A1 | 4/2009 | Gross et al. |
| 2009/0193996 | A1 * | 8/2009 | Brydges-Price ........ F42B 12/54 102/502 |
| 2009/0196907 | A1 | 8/2009 | Bunick et al. |
| 2009/0209903 | A1 * | 8/2009 | Cherif-Cheikh ........... A61M 37/0069 604/63 |
| 2010/0082015 | A1 | 4/2010 | Chebator |
| 2010/0198146 | A1 * | 8/2010 | Jagadeesh ........... A61M 5/3015 604/69 |
| 2011/0152755 | A1 * | 6/2011 | Schmalz .................. A61D 7/00 604/60 |
| 2011/0306929 | A1 | 12/2011 | Levesque et al. |
| 2012/0123324 | A1 * | 5/2012 | Schmalz ........... A61M 37/0069 604/63 |
| 2012/0197232 | A1 | 8/2012 | Lee et al. |
| 2013/0317477 | A1 | 11/2013 | Edwards et al. |
| 2014/0088555 | A1 * | 3/2014 | Li ........................ A61M 5/1684 604/67 |
| 2014/0254303 | A1 | 9/2014 | McArthur et al. |
| 2015/0126969 | A1 | 5/2015 | Mo |
| 2015/0314070 | A1 | 11/2015 | Heintz et al. |
| 2015/0374916 | A1 | 12/2015 | Bertolote et al. |
| 2016/0256095 | A1 | 9/2016 | Krasnow et al. |
| 2016/0256106 | A1 * | 9/2016 | Krasnow ............ A61B 5/15125 |
| 2016/0271381 | A1 * | 9/2016 | Falo, Jr. ................ B29C 39/025 |
| 2016/0361496 | A1 | 12/2016 | Guillermo et al. |
| 2017/0085183 | A1 | 3/2017 | Notsch |
| 2017/0119969 | A1 * | 5/2017 | McCullough ..... A61M 5/31568 |
| 2017/0290776 | A1 * | 10/2017 | Schobel ................. A61K 47/12 |
| 2018/0021556 | A1 * | 1/2018 | Lim ................... A61M 37/0015 604/57 |
| 2018/0093040 | A1 | 4/2018 | Thorne, Jr. et al. |
| 2018/0193563 | A1 | 7/2018 | Krasnow et al. |
| 2018/0287435 | A1 | 10/2018 | Wilson et al. |
| 2020/0009324 | A1 | 1/2020 | Barrows et al. |

FOREIGN PATENT DOCUMENTS

| | | |
|---|---|---|
| WO | 03068290 | 8/2003 |
| WO | 2014047657 | 3/2014 |
| WO | 2016130082 | 8/2016 |
| WO | 2021007351 | 1/2021 |
| WO | 2021007355 | 1/2021 |

OTHER PUBLICATIONS

CN201890000573.6, "Office Action", dated Jun. 19, 2020, 2 pages.
EP20162484.8, "Extended European Search Report", dated Apr. 28, 2020, 7 pages.
International Application No. PCT/US2018/012940, "International Preliminary Report on Patentability", dated Jul. 18, 2019, 11 pages.
U.S. Appl. No. 15/865,335 , Non-Final Office Action, dated Sep. 4, 2020, 17 pages.
Application No. CN201890000573.6 , Office Action, dated Sep. 10, 2020, 2 pages.
Application No. EP18150703.9 , Extended European Search Report, dated Mar. 14, 2018, 10 pages.
Application No. EP18150703.9 , Notice of Decision to Grant, dated Feb. 20, 2020, 2 pages.
Application No. PCT/US2018/012879 , International Search Report and Written Opinion, dated Apr. 11, 2018, 16 pages.
PCT/US2020/041255 , "Invitation to Pay Additional Fees and, Where Applicable, Protest Fee", Aug. 19, 2020, 2 pages.
U.S. Appl. No. 15/865,335 , Final Office Action, dated Feb. 9, 2021, 18 pages.
U.S. Appl. No. 16/122,981 , Non-Final Office Action, dated Oct. 19, 2020, 23 pages.
Application No. CN201890000573.6 , Notice of Decision to Grant, dated Dec. 8, 2020, 2 pages.
Application No. PCT/US2020/041255 , International Search Report and Written Opinion, dated Oct. 27, 2020, 13 pages.

(56) References Cited

OTHER PUBLICATIONS

U.S. Appl. No. 15/865,335, Advisory Action, dated Jun. 11, 2021, 3 pages.
U.S. Appl. No. 16/122,981, Final Office Action, dated Aug. 19, 2021, 23 pages.
Application No. PCT/US2020/041260, International Search Report and Written Opinion, dated Oct. 1, 2020, 11 pages.
Application No. EP18712708.9, Office Action, dated Jan. 18, 2022, 4 pages.
U.S. Appl. No. 15/865,335, Notice of Allowance, dated Mar. 15, 2022, 13 pages.

* cited by examiner

WEARABLE NON-LIQUID MEDICATION INJECTION DEVICE

CROSS-REFERENCE TO RELATED APPLICATIONS

This application claims priority to U.S. Provisional Application No. 62/505,457, filed May 12, 2017, entitled "Systems and Methods for Wearable Emergency Drug Injection Devices," and to U.S. Provisional Application No. 62/444,237, filed Jan. 9, 2017, entitled "Electronically-Actuated Drug Delivery System," which are both hereby incorporated by reference in their entirety herein.

FIELD OF THE INVENTION

The present disclosure relates to medication injection devices, and in particular to systems and methods for on-demand delivery of a non-liquid medication from a wearable medication injection device.

BACKGROUND

People with certain medical conditions may require medication in response to certain physiological conditions. Medical needles are widely used in the course of patient care and treatment, particularly with respect to the delivery of medication to a patient. In one common form, hollow hypodermic needles are employed for transcutaneous delivery of a selected medication from a syringe or the like. In another common form, insertion needles are employed for transcutaneous placement of a soft and relatively flexible tubular cannula, followed by insertion needle removal and subsequent infusion of medical fluid or medication to the patient through the cannula. For example, some people with diabetes may monitor their blood sugar to keep blood sugar levels as close to normal as possible without causing low blood sugar. Medications used to treat diabetes do so by lowering blood sugar levels. To respond to a high blood sugar, a person or health care provider may inject insulin, such as with a hypodermic needle or insertion needle for a tubular cannula, to help lower the blood sugar level.

Some people are reluctant or hesitant to pierce their own skin with a medical needle, and thus encounter difficulties in correct needle placement for proper administration of the medication. Such difficulties can be attributable to insufficient manual dexterity or skill to achieve proper needle placement or alternately to anxiety associated with anticipated discomfort as the needle pierces the skin. This problem can be overcome with automated medication delivery devices. In another common form, medical needles are provided in automated injectors for quickly and easily placing an insertion needle through the skin of a patient at the correct insertion angle, and with a speed and force of insertion which minimizes patient discomfort. For example, some people have a severe allergy to allergens such as peanuts or insect stings and may experience anaphylaxis as a result of contact with the allergen. Epinephrine (adrenaline) is the primary treatment for anaphylaxis with no absolute contraindication to its use. To respond to the anaphylaxis, the person or health care provider may inject epinephrine, such as with an off-the-shelf automated injector, e.g., an EpiPen®, to stop the anaphylaxis.

Although automated injectors such as the EpiPen® are capable of automatically placing an insertion needle through the skin of a patient at the correct insertion angle to deliver a medication, there is still a requirement for manual intervention by the patient or healthcare provider (e.g., someone must still position the injector on the skin and activate the trigger for injection). However, during an emergency, a user may not have the capacity to seek help or self-administer a medication. It thus may be equally life-saving to have a wearable medication injection device that can deliver a medication on-demand when the device receives a signal that the user is in need of the medication.

A major challenge to the on-demand delivery of the medication from the medication injection device is that the device needs to be worn, and should be able to maintain discreet footprint on the patient, i.e., a small overall size and low profile, in order to maintain customer satisfaction. However, many medications such as glucagon are typically stored as a 1 mL solution (liquid solution or dry-liquid mixture solution) in one or more chambers of the medication injection device, which takes up a significant portion of the overall size of the medication injection device. Therefore, the ability to minimize the space taken up by the storage of the medication, is important for the success of the wearable medication injection device. Furthermore, optimizing automated on-demand delivery of the medication is important for overall treatment of the medical condition and adoption of such a delivery device. Accordingly, the need exists for systems and methods that have the capability for automated on-demand delivery of a medication from a wearable medication injection device.

BRIEF SUMMARY

One general aspect includes a device for injecting an injectable substance into a user, including: a housing defining a chamber having a first end and a second end. The device also includes a piston disposed towards the first end of the chamber and translatable within the chamber. The device also includes a hollow needle disposed within the chamber and extending from in front of the piston towards the second end of the chamber. The device also includes an energetic material disposed within the first end of the chamber and behind the piston to force the piston and hollow needle towards the second end of the chamber in response to activation of the energetic material. The device also includes a medication strip disposed within the hollow needle and including the injectable substance.

Implementations may include one or more of the following features. The device where the medication strip includes one or more polymers and the injectable substance is in a non-liquid form that is at least one of: (i) disposed on a surface of the one or more polymers, and (ii) imbibed within the one or more polymers. The device further including a spring disposed within the chamber and extending from in front of the piston towards the second end of the chamber. The device further including a back hub attached to an end of the medication strip and disposed within the chamber and in front of the piston. The device further including a catch feature disposed at the second end of the chamber, where the catch feature includes a mating structure to engage and lock the back hub in place at the second end of the chamber once the piston is forced towards the second end of the chamber in response to activation of the energetic material. The device further including: an opening in the housing to an external environment. The device may also include a needle guide that defines a curved path that forces the hollow needle to bend towards the opening. The device further including a reusable portion including: a firing circuit and a receiver, where the firing circuit is connectable to the energetic material and configured to activate the energetic material upon receiving an activation command from the receiver. Implementations of the described techniques may include hardware, a method or process, or computer software on a computer-accessible medium.

Another general aspect includes a device for injecting an injectable substance into a user, including: a first portion including a firing circuit; and a second portion connected to the first portion. The second portion includes a chamber. The second portion also includes a piston disposed within the chamber. The second portion also includes a needle disposed within the chamber on a first side of the piston. The second portion also includes an energetic material disposed within the chamber on a second side of the piston and connected to the firing circuit. The second portion also includes a medication strip disposed within the needle, where the medication strip includes the injectable substance in a non-liquid form.

Implementations may include one or more of the following features. The device where the first portion further includes a battery and one or more capacitors, the battery is configured to store a charge in one or more capacitors, and the firing circuit is configured to: (i) activate the energetic material by coupling the one or more capacitors to an activator in contact with the energetic material, and (ii) release the stored charge and initiate an exothermic reaction of the energetic material. The device where the medication strip includes one or more polymers and the injectable substance is at least one of: (i) disposed on a surface of the one or more polymers, and (ii) imbibed within the one or more polymers. The device where the injectable substance includes epinephrine or glucagon. The device further including a spring disposed within the chamber on the first side of the piston. The device further including a back hub attached to an end of the medication strip and disposed within the chamber on the first side of the piston. The device further including a catch feature disposed within the chamber on the first side of the piston, where the catch feature includes a mating structure to engage and lock the back hub in place once the piston is forced to traverse the chamber in response to activation of the energetic material. The device further including an opening in the second portion to an external environment. The device may also include a needle guide that defines a curved path that forces the needle to bend towards the opening, where the needle includes a hollow tube having one pointed end with an opening. Implementations of the described techniques may include hardware, a method or process, or computer software on a computer-accessible medium.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method for delivering an injectable substance to a user, including receiving, at a first circuit, a command to deliver the injectable substance. The method also includes activating an energetic material disposed within a chamber of an injection device to initiate an exothermic reaction that forces a piston to traverse the chamber and drive a needle outside of the injection device into the user, where a medication strip is disposed within the needle and includes the injectable substance in a non-liquid form. The method also includes retracting the needle into the chamber from outside of the injection device, where the medication strip remains in the user upon retracting the needle. The method also includes delivering the injectable substance to the user. Other embodiments of this aspect include corresponding computer systems, apparatus, and computer programs recorded on one or more computer storage devices, each configured to perform the actions of the methods.

Implementations may include one or more of the following features. The method where: the medication strip includes one or more polymers and the injectable substance is at least one of: (i) disposed on a surface of the one or more polymers, and (ii) imbibed within the one or more polymers. The method may also include the injectable substance is delivered to the user by way of passive diffusion of the injectable substance from the medication strip into the user. The method where initiating the exothermic reaction causes pressure to increase behind the piston, which eventually surpasses a force of a spring within the chamber, causing the spring to compress and the piston to traverse the chamber. The method where the retracting the needle includes releasing the pressure behind the piston such that when the force of the spring ultimately surpasses the pressure, the piston traverses the chamber causing the needle to retract into the chamber. The method where when the piston traverses the chamber and drives the needle outside of the injection device, the piston transports a back hub attached to an end of the medication strip through the chamber and into contact with a catch feature that engages the back hub, and engagement of the catch feature with the back hub allows for the medication strip to remain in the user upon retracting the needle. Implementations of the described techniques may include hardware, a method or process, or computer software on a computer-accessible medium.

BRIEF DESCRIPTION OF THE DRAWINGS

The present invention will be better understood in view of the following non-limiting figures, in which.

DETAILED DESCRIPTION

I. Introduction

As discussed herein, a problem associated with conventional medication injection devices is that they typically require some form of manual control (e.g., holding the device during injection), and the inject medications are typically stored as a bulky liquid solution. These limitations are detrimental to a fully autonomous medication injection device that can be worn by a user. To address these problems, various embodiments of systems and/or methods described herein are directed toward a connected wearable medication injection device that can inject a substance or medication on-demand in a non-liquid form such that a liquid solution is not necessary and the overall size and profile of the medication injection device may be decreased.

As used herein, the "injectable substance" or "medication" comprises any desired pharmaceutical agent or mixture of individual pharmaceutical agents or the like, for the administration of one or more active agents to a region of a patient. For example, suitable injectable substances or medications may include epinephrine, glucagon or a glucagon activation solution, or other drugs or chemicals. As used herein, "non-liquid" means a substance that is not a liquid. For example, a non-liquid form may be a substance in a solid form, e.g., a dry powder medication. A medication injection device is a device or system having electronic circuit components and/or software configured to deliver the non-liquid substance to a specific site (e.g., a subdermal or subcutaneous) of the patient via an injectable needle.

One or more portions of the medication injection device may be worn on a patient's body. For example, a user with a medical condition, such as diabetes or a severe allergy to a substance, may use a wearable medication injection device according to this disclosure. In this example, the user (also the "wearer") obtains the device, which is about 20 mm wide, about 25 mm long, and about 1 cm height. The example device has two halves that connect together to form a completed device. The first half may be disposable and has components to store and deliver a dose of an injectable substance, e.g., 1 mg of medication powder. Specifically, the first half comprises a piston, a spring, an energetic material, and a hollow needle. Within the needle is a small detachable strip that is about 100 um in width, about 50 um in thickness, and about 5 mm in length and contains the injectable substance such as a dry form of a medication (as used herein when combined, a "medication strip"). The medication strip is held at the back end by a hub. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

The second half of the device, the reusable half in this example, includes circuitry to receive a command to inject the injectable substance and to activate the energetic material in response to the command. For example, the wearer could press a button on the reusable half to trigger the circuitry to activate the charges. Alternatively, the circuitry could receive the command wirelessly from another device, such as the wearer's smartphone, continuous glucose monitor, a biosensor, insulin pump, etc. In this example, the circuitry is configured to activate the energetic material on-demand, for example in response to a signal received from a continuous glucose monitor. The energetic material may be activated by heating the energetic material, which causes a highly exothermic reaction that rapidly releases gas and heat. The spike in pressure from the exothermic reaction forces the piston towards the end of the device and drives the hollow needle and medication strip into the wearer. When the needle and medication strip meet the end of travel, the needle is retracted via the spring, and the hub of the medication strip engages with a feature at an end of the device, forcing the medication strip to remain in place inside the wearer. While the medication strip is inside the wearer, the medication will passively elute into the wearer. When finished, the wearer may pull off the device, and the medication strip will naturally pull out with the device Advantageously, these approaches provide a medication injection device that has a small overall size and low profile, which is possible because the conventional liquid holding chambers are removed from the device and replaced with a medication strip that is stored in the hollow needle. Moreover, these approaches allow for on-demand medication delivery without user interaction (fully automated). Also advantageously, medications may be multiplexed on the medication strip to deliver "cocktails of active agents". For example, a portion of the strip may comprise glucagon and a second portion of the strip may comprise an activator for glucagon, which can be simultaneously delivered to a region of interest, to enable the glucagon to be metabolized by the wearer. Further, the medication strip described herein can make the medication injection device personalized to each individual patient.

II. Medication Injection Devices or Systems

Figure 1:
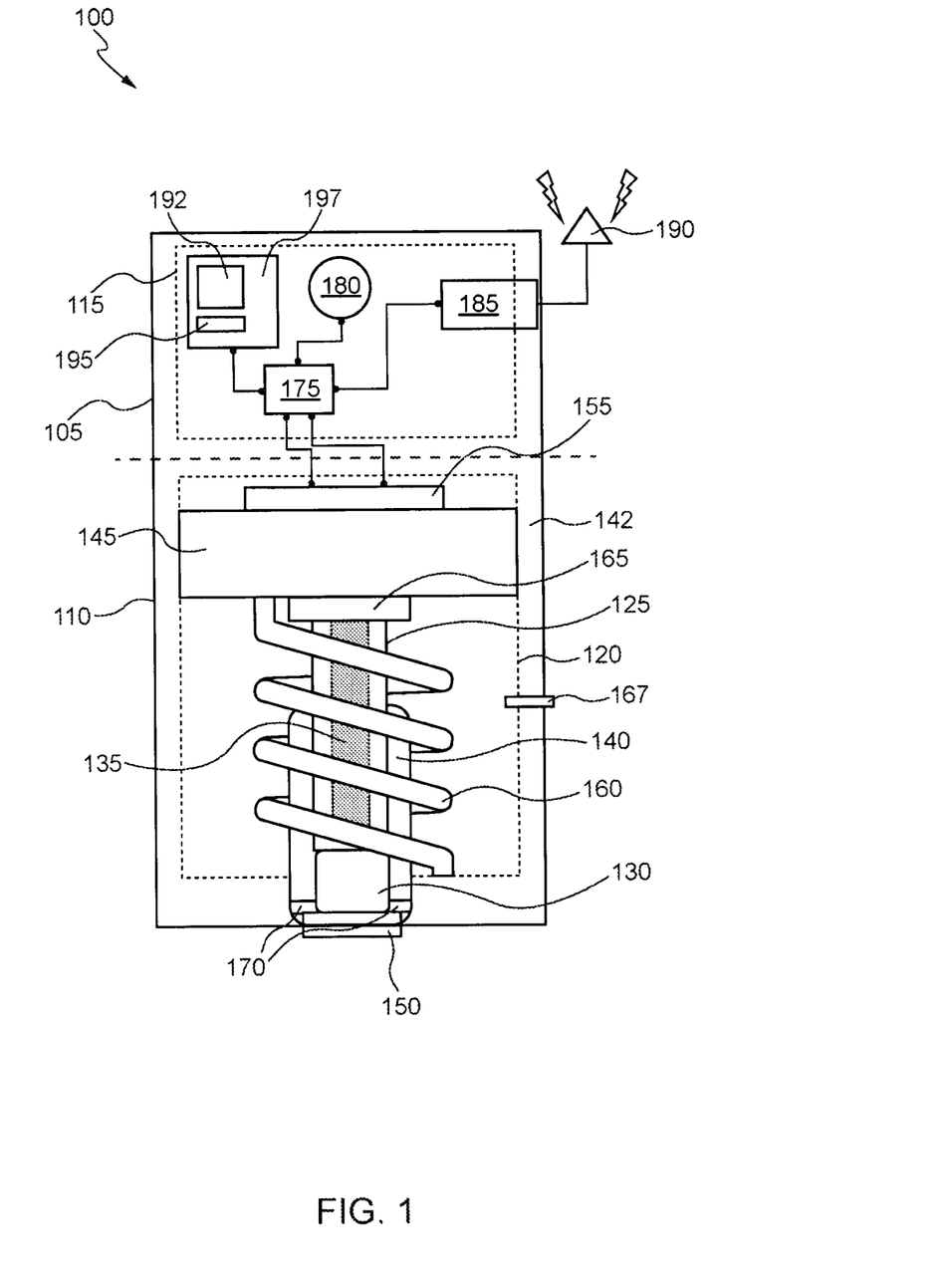
FIG. 1 shows a block diagram of a medical injection device in accordance with various embodiments.

FIG. 1 shows a block diagram of a medical injection device 100 in accordance with various aspects. In various embodiments, the device 100 includes two portions 105 and 110 that are connected, but are separable from each other. The first portion 105 comprises electronic components 115 that may be separable from the second portion 110 to allow for re-use of the electronics components 115. The second portion 110 comprises a chamber 120 that houses an injector comprising a needle 125 such as a hollow needle. In some embodiments, the needle 125 comprises a hollow tube with a sharp tip at one end that contains a small opening (e.g., completely open, slotted, or partially opened) and a blunt tip at the other end that is either open or closed. The injector can be used to drive the needle 125 optionally through a needle cap 130 and into a user's skin. Within the needle 125 is a detachable medication strip 135 that is about 15 μm to 150 μm in width, e.g., 100 μm in width, about 25 μm to 75 μm in thickness, e.g., about 50 μm in thickness, and about 2.0 mm to 7.5 mm in length, e.g., 5 mm in length, and contains the injectable substance such as a dry form of a medication.

In some embodiments, the strip 135 is comprised of one or more polymers such as polysiloxanes, polytetrafluoroethylene (PTFE), polyether ether ketone (PEEK), polylactic acid (PLA), polyglycolic acid (PGA), polycaprolactone (PCL), polyethylene and cyclic olefin copolymers (COCs), perfluoroether (PFA), fluorinated ethylene propylene (FEP), polyimide, and polyesters. As discussed herein, the injectable substance comprises any desired pharmaceutical agent or mixture of individual pharmaceutical agents or the like, for the administration of one or more active agents to a region of the user. For example, suitable injectable substances or medications may include epinephrine, glucagon or a glucagon activation solution, or other drugs or chemicals. The injectable substance of the strip 135 is in a non-liquid form that is at least one of: (i) disposed on a surface of the one or more polymers, and (ii) imbibed within the one or more polymers. For example, during manufacture of the strip 135, a medication may be immobilized onto a strip of polymer by depositing the injectable substance in liquid form onto a surface of the polymer and/or imbibing the injectable substance into the polymer to create an intermediate assembly (a polymer strip and injectable substance in liquid form), and the intermediate assembly is then freeze-dried using standard lyophilization methods to create a final assembly or medication strip (strip 135).

In some embodiments, the injectable substance may include a plurality of medications that are multiplexed on the medication strip to deliver "cocktails of active agents". For example, a portion of the strip may comprise glucagon and a second portion of the strip may comprise an activator for glucagon, which can be simultaneously delivered to a region of interest, to enable the glucagon to be metabolized by the wearer. Further, the strip 135 can have various dosages and/or types of medications that are individualized for the user of the device 100, and thus make the device 100 personalized to the user. In certain embodiments, because the needle 125 is hollow, the strip 135 can be stored in the needle 125 within chamber 120. Upon actuation of the injection mechanism, the strip 135 is forced into the user via the needle 125. While the strip 135 is inside the wearer, the injectable substance may passively elute into the wearer. The second portion 110 may be discarded after delivering the injectable substance into the wearer.

In some embodiments, the device 100 is designed to be worn flush against a wearer's body, such as on an upper arm or torso. With respect to description of length, width, and height, the height of the device 100 refers to how far the device 100 extends above the wearer's skin when worn. The length and width, by contrast, refer to the dimensions of the perimeter of the device 100. In certain embodiments, the device 100 is about 15 mm to 30 mm wide, e.g., 20 mm wide, about 15 mm to 35 mm long, e.g., 25 mm long, and about 0.5 cm to 3 cm thick, e.g., 1 cm thick. The needle 125 may be oriented to extend parallel to the wearer's skin; however, a needle guide 140 defines a curved path that forces the needle 125 to bend towards the wearer's skin at an angle departing from its initial orientation by approximately 30 degrees, 35 degrees, 40 degrees, or 45 degrees. In some embodiments, the needle 125 is formed of a flexible material(s), such as a nickel-titanium alloy (e.g., Nitinol), to allow the needle 125 to bend at angles of up to 45 degrees (or more) without breaking or obstructing a travel path of the strip 135 through the interior of the needle 125. In certain embodiments, the needle 125 is a 22-gauge needle, 23-gauge needle, or a 25-gauge needle. Such a device size and needle size provide a mechanism suitable for injecting the strip 135 into the wearer while providing a device 100 that maintains a small size with a low profile and causes a tolerable amount of discomfort; however, other suitable device sizes and needle sizes and diameters may be employed.

In various embodiments, a housing 142 of the second portion 110 defines the chamber 120 that houses the injector. The injector may further comprise a piston 145 that is initially positioned at a first end of the chamber 120 opposite an opening 150 of the housing 142 to an external environment. In some embodiments, the chamber 120 is in fluid communication to the opening 150. In other embodiments, the chamber 120 is closed off from the opening 150 by the needle cap 130. The piston 145 is translatable within the chamber 120 (e.g., moveable from the first end towards a second end of the chamber). The needle 125 extends from in front of the piston 145 towards the second end of the chamber (the end near the opening 150). In some embodiments, the needle 125 is attached to a front surface of the piston 145. Consequently, when the piston is activated and moves toward the opening 150, the needle 125 and the strip 135, which are located in front of the piston 145, are forced optionally through the needle cap 130 and the opening 150. The piston 145 may be sized to have approximately the same cross-sectional area as the chamber 120 to prevent the contents of the chamber 120 from sliding around the piston 145 or, as described herein, gas pressure generated behind the piston 145 from being dissipated by escaping around the piston 145. In addition, in some embodiments, the piston 145 has one or more seals attached around a perimeter of the piston 145 to prevent such leakage of material or gasses past the piston 145.

The injector may further comprise an energetic material 155 (e.g., a propellant) disposed behind the piston 145 and connected to one or more of the electronic components 115 in the first portion 105. When the energetic material 155 is activated via the one or more of the electronic components 115, the energetic material 155 may undergo an exothermic reaction and generate pressure within a portion of the chamber 120 behind the piston 145, thereby forcing the piston 145 towards the second end of the chamber 120 with the opening 150. In some embodiments, the energetic material 155 comprises a nitrocellulose material. In certain embodiments, the energetic material 155 can be modified to create a faster-burning or slower-burning material based on device 100 design. For example, the energetic material 155 may be a nitrocellulose material in a cotton-based format for faster-burning or in a paper-based format for a slower-burning format. Selection of an appropriate energetic material may be made based on size and constituents of the chamber 120, needle 125, strip 135, piston 145, and/or spring 160.

The injector may further comprise the spring 160 disposed with in the chamber 120 and extending from in front of the piston 145 towards the second end of the chamber (the end near the opening 150). In some embodiments, the spring 160 abuts a front surface of the piston 145. The spring 160 may be provided (optionally coupled to the needle cap 130) to hold the piston 145 in place within the chamber 120 (e.g., abutting the energetic material 155) and enable retraction of the needle 125 once the energetic material 155 propels the piston 145 towards the second end of the chamber 120. For example, the pressure generated by the energetic material 155 may initially overcome a force of the spring 160, but as the gasses from the exothermic reaction dissipate, e.g., via an exhaust port 167, the pressure within the chamber 120 drops and the spring 160 may ultimately overcome the pressure and retract the needle 125. In some embodiments, when the needle 125 and the strip 135 meet their end of travel into the wearer, the needle 125 is retracted via the spring 160. In additional or alternative embodiments, other needle retraction mechanisms may be employed, such as another propellant charge located beneath the needle cap 130.

In some embodiments, a back hub 165 is attached to an end of the strip 135 and initially disposed within the chamber 120 and in front of the piston 145. Additionally, a catch feature 170 is disposed at the second end of the chamber 120. The catch feature 170 includes a mating structure such as a clip to engage and lock the back hub 165 in the place at the second end of the chamber 120 once the piston 145 is forced towards the second end of the chamber 120 in response to activation of the energetic material 155. Attachment of the back hub 165 to the end of the strip 135 and the catch feature 170 allows for the strip 135 to remain in place inside the wearer during and after retraction of the needle 125.

While the second portion 110 includes the mechanisms for storing and injecting the strip 135, the first portion 110 includes components to receive a command (or commands) to initiate the exothermic reaction of the energetic material 155 and eventually drive the strip 135 into the wearer. In various embodiments, the first portion 110 includes a firing circuit 175, a battery 180 or other electrical power source or connection, a wireless receiver 185, and an antenna 190. To initiate the exothermic reaction of the energetic material 155, a command may be received via the antenna 190 and the receiver 185 from a remote device, such as the wearer's smartphone or a biosensor (e.g., a continuous glucose monitor), and the command may be relayed to the firing circuit 175. In response to receiving the command, the firing circuit 175 may apply a signal, voltage, or current to the energetic material 155 using power supplied by the battery 180. In some embodiments, the energetic material 155 is activated by an electrical discharge. For example, to supply the electrical discharge, the firing circuit 175, prior to receiving the command, charges one or more capacitors using the battery 180. Upon receiving the command from the receiver 185, the firing circuit 175 couples the capacitor(s), optionally in sequence, to an activator (e.g., electrical leads or a conductive contact) in contact with the energetic material 155, thereby allowing the capacitor(s) to discharge and initiate the exothermic reaction of the energetic material 155.

In addition to the firing circuit 175, battery 180, and receiver 185, other electronic components may be provided within the first portion 110 as well, such as battery charging circuitry 192, power and filtering circuitry 195, and a microcontroller 197, e.g., an ASIC defined on a field-programmable gate array ("FPGA"). Still further electronic components may be included within the first portion 110 to enable various features according to this disclosure. While the embodiments discussed herein employ a wireless command to activate the firing circuit 175, it should be understood that it has been contemplated that the device 100 may instead have a wired connection to another device, e.g., a biosensor, or may have a button or other wearer manipulatable device ("manipulandum") to activate the firing circuit 175. Further, while the embodiments shown in FIG. 1 have two portions 105, 110 that may be decoupled from each other, in some examples, the device 100 may be formed from a single portion that includes the components described above, or other components according to this disclosure. Thus, rather than providing a second portion 110 that is disposable and first portion 105 that is reusable, the entire device may be reusable or discarded.

Figure 2:
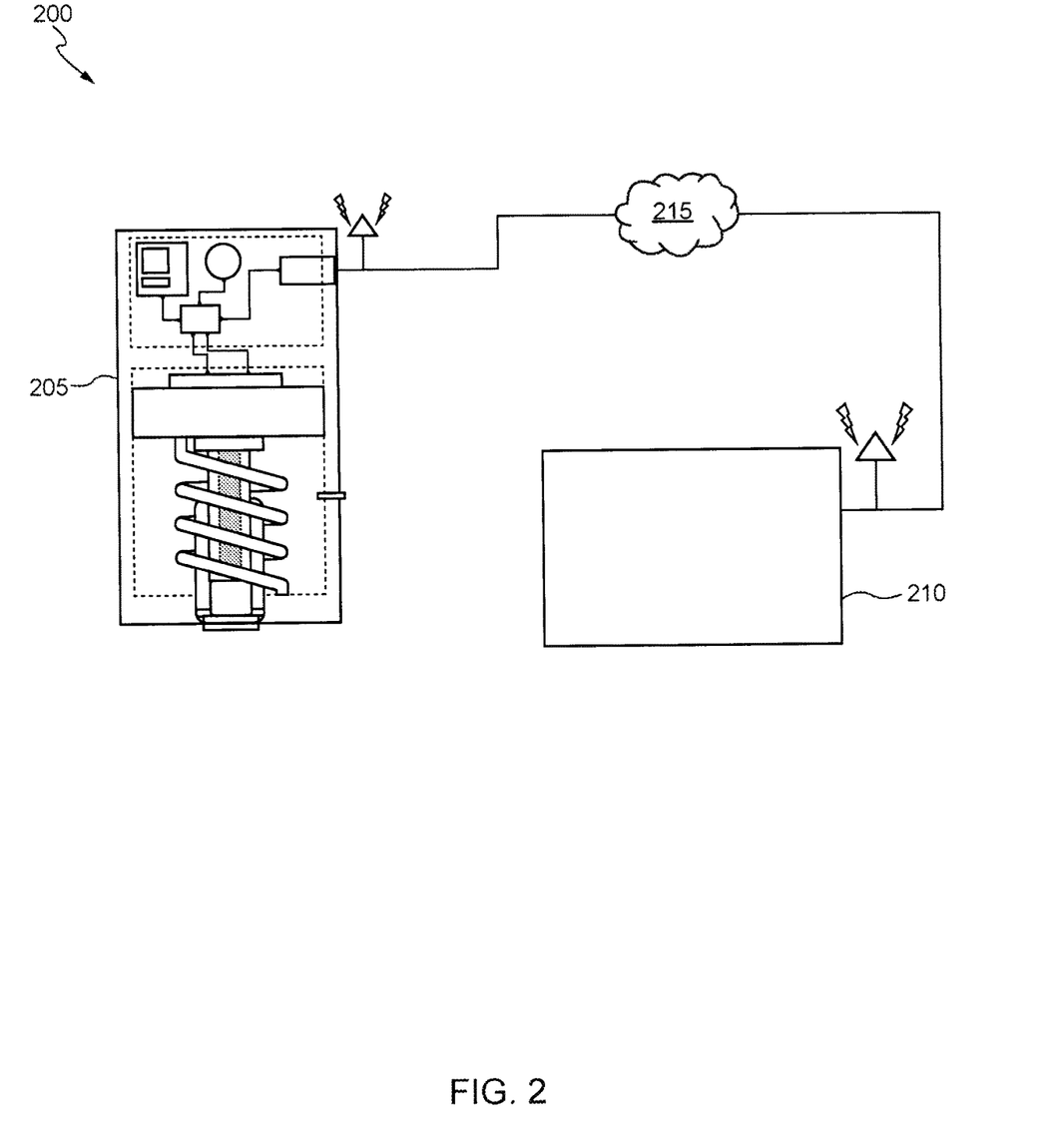
FIG. 2 shows a block diagram of an example system for controlling a medical injection device in accordance with various embodiments.

FIG. 2 shows a block diagram of an example system 200 for controlling a medical injection device 205 (e.g., medical injection device 100 as discussed with respect to FIG. 1). In various embodiments, the device 205 is in communication with a remote device 210 via communication link 215 such that at least the remote device 210 can send a signal and the device 205 can receive the signal (in other embodiments, both the device 205 and the remote device 210 can send and receive signals). The remote device 210 may be any suitable device with a wireless transmitter, such as a smartphone, smartwatch, blood pressure sensor, continuous glucose monitor, etc. Such remote devices may be handheld or wearable devices or larger devices, such one or more sensing systems as may be found in a hospital or other medical office. The communication link 215 may be any suitable wireless or wired means of communication between two devices such as Bluetooth®, Bluetooth® low-energy ("BLE"), wireless networking technology (e.g., Wi-Fi), near-field communications ("NFC"), etc. While the device 205, the remote device 210, and communication link 215 are described herein as a wearable system with respect to several described embodiments, it should be understood that various systems and arrangements comprising the device 205, the remote device 210, and communication link 215 are contemplated without departing from the spirit and scope of the present disclosure. For example, the system 200 may include the device 205 and the remote device 210 within a distributed environment such as a cloud computing environment, and the device 205 and the remote device 210 may be in communication via one or more communication networks. Examples of communication networks include, without restriction, the Internet, a wide area network (WAN), a local area network (LAN), an Ethernet network, a public or private network, a wired network, a wireless network, and the like, and combinations thereof.

In some embodiments, the remote device 210 is a continuous glucose monitor that senses and stores glucose levels over time for the wearer. The glucose levels may be accessed wirelessly by various devices, such as the wearer's smartphone, an insulin pump, or example wearable drug injection devices according to this disclosure. The device 210 may be configured with one or more glucose level thresholds, below which the wearer is experiencing a hypoglycemic event and above which the wearer is experiencing a hyperglycemic event. The device 210 may periodically measure the wearer's glucose levels and compare them to the one or more glucose level thresholds. If a measured glucose level (or several consecutive measured glucose levels) exceeds one or more of the glucose level thresholds, the device 210 may determine a hyperglycemic or hypoglycemic event. The device 210 may issue an alert to the wearer, such as by transmitting a signal to the wearer's insulin pump to trigger an audible alarm and, in the instance of a hyperglycemic event, trigger insulin delivery. In the instance of a hypoglycemic event, the device 210 may also transmit a signal (e.g., a command signal) to the device 205 to cause the injection mechanism to deliver a dose of glucagon to the wearer. For example, the device 210 may first transmit a signal to the wearer's insulin pump, if the wearer has one, and continue to monitor the wearer's glucose levels to detect whether the wearer's glucose levels continue to exceed one or more glucose level thresholds. If glucose levels do not continue to exceed one or more of the glucose level thresholds, then the device 210 may determine that appropriate action has been taken to alleviate the hypoglycemic event (e.g., the wearer has eaten something). However, if after a predetermined period of time, e.g., 5 minutes, the hypoglycemic event continues or worsens, the device 210 may then determine that intervention is needed and transmit the signal to the device 205 to cause a dose of glucagon to be injected into the wearer. Such an example may be desirable as it may allow the wearer to raise their glucose levels, even if they are unresponsive, e.g., due to being asleep or unconscious. And while this example relates to a hypoglycemic event and a continuous glucose monitor, other biosensors may be employed as well or instead for other pathologies and means for treatment. For example, blood pressure, electrocardiography, blood oxygen, etc. biosensors may be employed in some examples to detect medical events, such as anaphylaxis, etc., which may then trigger the biosensor, or another device such as a smartphone, to transmit a signal to the device 205 to cause an injectable substance, e.g., epinephrine, etc., to be injected into the wearer. Thus, different medical events may be addressed or mitigated automatically via the combination of the remote device 210 and the wearable drug injection device 205, which may address an emergency condition or may allow time for a full medical response to occur, if needed.

Figure 3A:
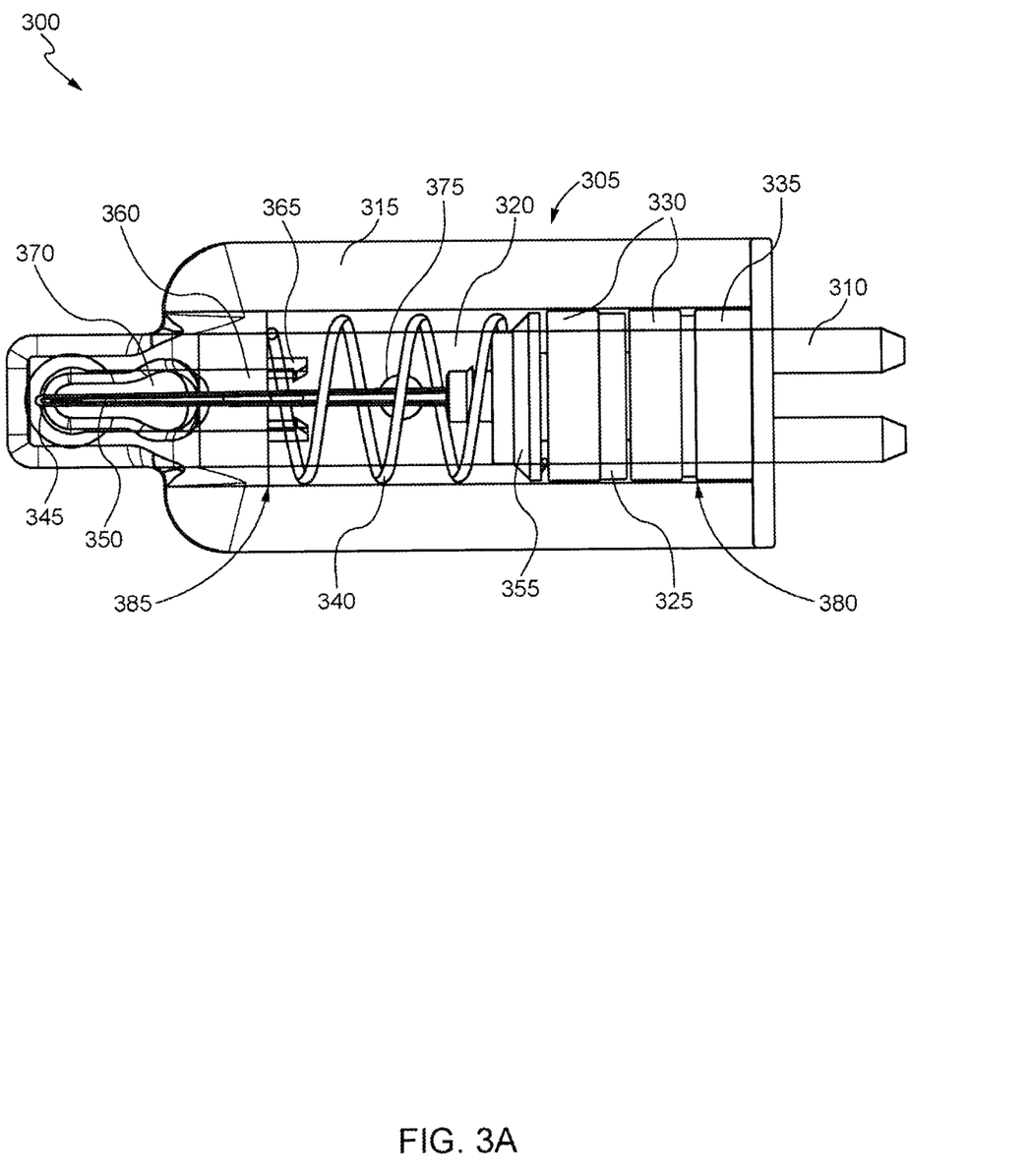
FIGS. 3A-3K show different views and phases of an example wearable medical injection device in accordance various embodiments.

Referring now to FIGS. 3A-3K, these figures show different views and phases of an example wearable medical injection device 300. In particular, FIG. 3A shows a disposable portion 305 (e.g., second portion 110 discussed with respect to FIG. 1) of the wearable medical injection device 300 that is connectable to a reusable portion (e.g., the first portion 105 discussed with respect to FIG. 1). As shown, the reusable portion may be releasably coupled to the disposable portion 305 by a connector 310. The connector 310 may comprise a plug and/or clips that engage with the reusable portion to releasably secure the disposable portion 305 and the reusable portion together. In various embodiments, a housing 315 of the disposable portion 305 defines a chamber 320 comprising a piston 325 with one or more sealing rings 330, an energetic material 335, a spring 340, a needle 345, a medication strip 350, a back hub 355, a needle guide 360, and a catch feature 365. The chamber may have an opening 370 to allow the needle 345 and strip 350 to exit the device 300 by way of the needle guide 360, and an exhaust port 375 to allow gasses generated by the energetic material 335 to escape from the chamber 320. While FIG. 3A illustrates, the exhaust port 375 releases gasses directly into the wearer's environment, in some examples, the exhaust port 375 may vent exhaust gasses into a needle retraction mechanism.

As shown in FIGS. 3A, 3C, 3F, and 3I, during a storage phase of the injectable substance, the energetic material 335 (e.g., a propellant) may be disposed behind the piston 325 and connected to one or more of the electronic components in the first portion via at least a portion of the connector 310 (e.g., conductive material of the connector). The spring 340 has a sufficient amount of force that it can hold the piston 325 adjacent to the energetic material 335 at a first end 380 of the chamber 320 during the storage phase. The spring 340 may be constructed from one or more materials such as iron, carbon, silicon, manganese, and chromium. The exact composition of the spring 340 depends on the properties required for the device 300, which may include the loads the spring 340 will need to withstand, how many cycles of stresses and strain the spring 340 will undergo, the temperatures the spring 340 has to operate under, whether the spring 340 needs to withstand heat or corrosion, how "plastic" (easy to shape) the spring 340 needs to be during its initial manufacture and shaping, etc.

Figure 3B:
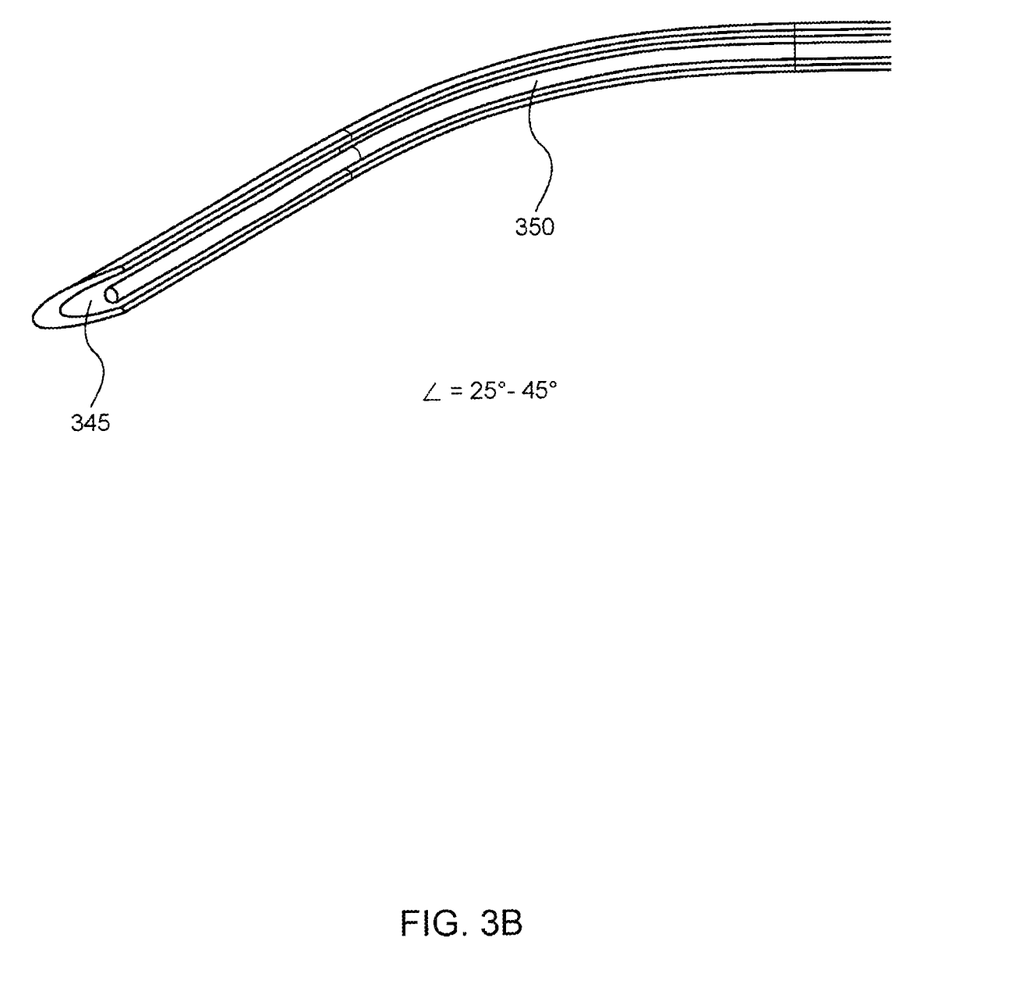

As further shown in FIGS. 3A, 3C, 3F, and 3I, during the storage phase of the injectable substance, the needle 345, the strip 350, and the back hub 355 may be disposed within the chamber 320. The back hub 355 is attached to an end of the strip 350 and may be positioned adjacent to the piston 325 towards the first end 380 of the chamber 320. At this position, the back hub 355 is not engaged with the catch feature 365. The needle 345 may be attached to the piston 325 through an opening in the back hub 355. The needle 345 may be oriented in the chamber 320 to extend parallel to the wearer's skin; however, the needle guide 360 defines a curved path that forces at least a portion of the needle 345 to bend towards the wearer's skin (e.g., C-shaped bend) during the storage phase at an angle departing from its initial orientation by approximately 25 degrees, 30 degrees, 35 degrees, 40 degrees, or 45 degrees. As shown in FIG. 3B, the needle 345 may be hollow to allow the strip 350 to be stored within the needle 345 and to be transported through the needle 345 into the wearer. In some embodiments, the needle 345 comprises a hollow tube with a sharp tip at one end that contains an opening (e.g., completely open, slotted, or partially opened) and a blunt tip at the other end that is either open or closed. The opening in the needle 345 allows for the strip 350 to be loaded into the needle 345 (for storage) and for the strip 350 to be delivered to a user (injected into a user from within the needle 345). In addition, the needle 345 may be constructed from a flexible material, such as a suitable plastic or metallic material (e.g., Nitinol). The needle 345 in this example is sufficiently flexible that it can bend at an angle of between 25 to 45 degrees without permanently deforming and while maintaining an unimpeded path through the needle 345. The needle guide 360, as shown in FIGS. 3C-3H, is formed or coupled to the opening 370 to provide a path through which the needle 345 is forced to bend at an angle towards the wearer's skin. Thus, as the needle 345 is driven by the piston 325, the needle 345 moves into and through the path formed in the needle guide 360 and bends towards the wearer's skin.

Figures 3C, 3D, 3E, 3F, 3G, 3H:
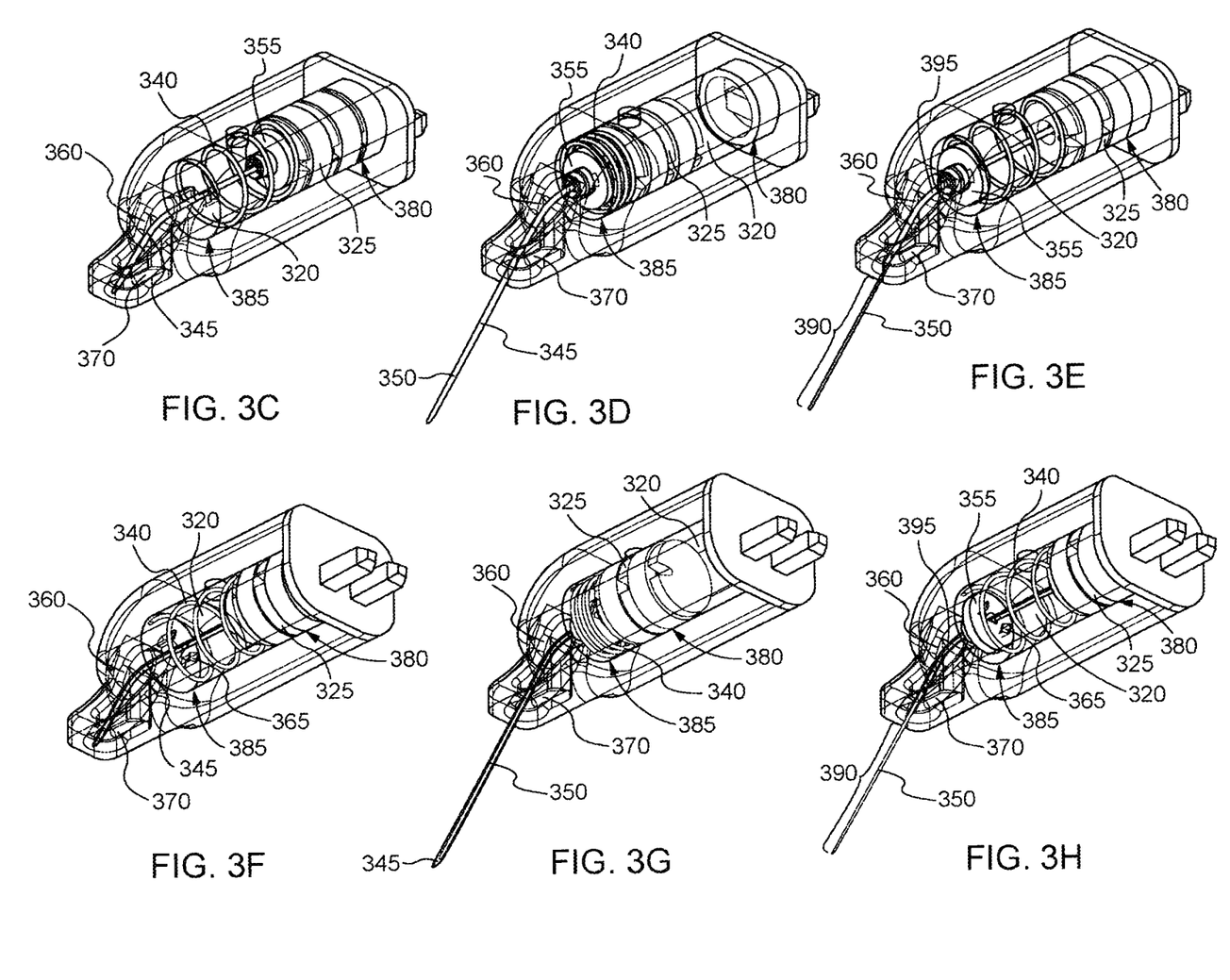
Figure 3I:
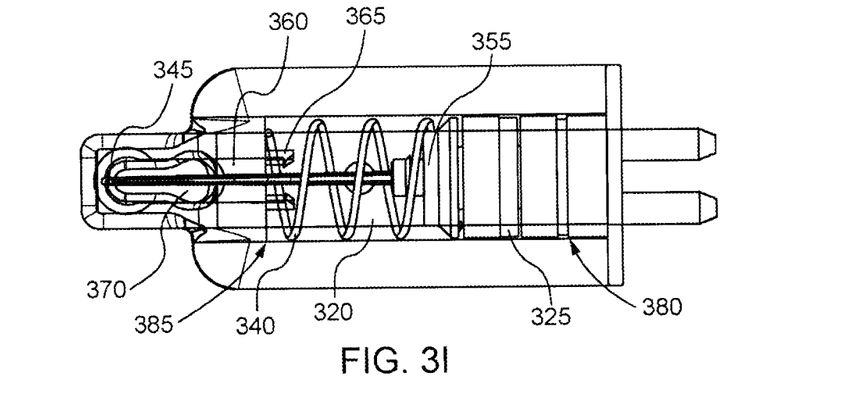
Figure 3J:
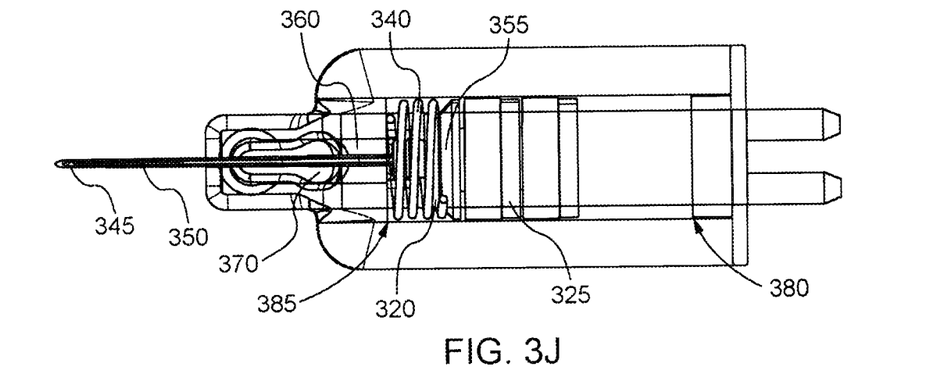

Upon receiving the command signal from the receiver, the firing circuit activates the exothermic reaction of the energetic material 335 and the piston 325 is driven from the first end 380 of the chamber 320 to a second end 385 such that the needle 345 and strip 350 are driven out of the opening 370 into the wearer's skin. As shown in FIGS. 3D, 3G, and 3J, during the injection phase of the injectable substance, the needle 345 and the strip 350 are driven out of the opening 370 into the wearer's skin via the needle guide 360, and the back hub 355 remains attached to an end of the strip 350 but disposed at the second end 385 of the chamber 320. At this position, the back hub 355 is engaged with the catch feature 365. In certain embodiments, the catch feature 365 is a clip with two hooks for engaging a lip of the back hub 355, and thus holding the back hub 355 at the second end 385 of the chamber 320. The spring 340 is compressed at the second end 385 of the chamber 320 by the pressure generated by the exothermic reaction of the energetic material 335.

Figure 3K:
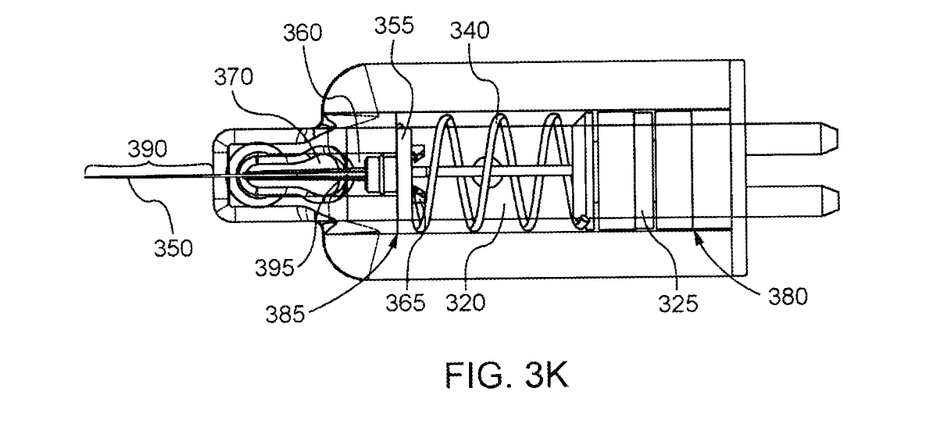

Once the strip 350 has been expelled out of the device 300 and into the wearer via the needle 345, the device 300 may retract the needle 345 via the spring 340. For example, the pressure generated by the energetic material 335 may initially overcome a force of the spring 340, but as the pressure dissipates, e.g., via the exhaust port 375, the spring 340 may ultimately overcome the pressure and retract the needle 345. In additional or alternative embodiments, other needle retraction mechanisms may be employed, such as another propellant charge located beneath a needle cap. As shown in FIGS. 3E, 3H, and 3K, during the delivery phase of the injectable substance, the needle 345 is retracted back into the chamber 320 and the piston 325 may be positioned once more at the first end 380 of the chamber 320. For example, the spring 340 has a sufficient amount of force that it can hold the piston 325 adjacent to the energetic material 335 at the first end 380 of the chamber 320 during the delivery phase. Additionally, a first portion 390 of the strip 350 remains outside of the device and inside the wearer. A second portion 395 of the strip 350 remains attached to the back hub 355, which remains engaged with the catch feature 365, such that the strip 350 is not retracted with the needle 345. While the first portion 390 of the strip 350 is inside the wearer, the injectable substance may passively elute into the wearer. Once the injectable substance has been delivered, the wearer may pull off the device 300, and the strip 350 will naturally pull out of the wearer due to the attachment of the strip 350 with the back hub 355 and the attachment of the back hub 355 with the housing 315 via the catch feature 365.

III. Methods for Delivering a Medication

Figure 4:
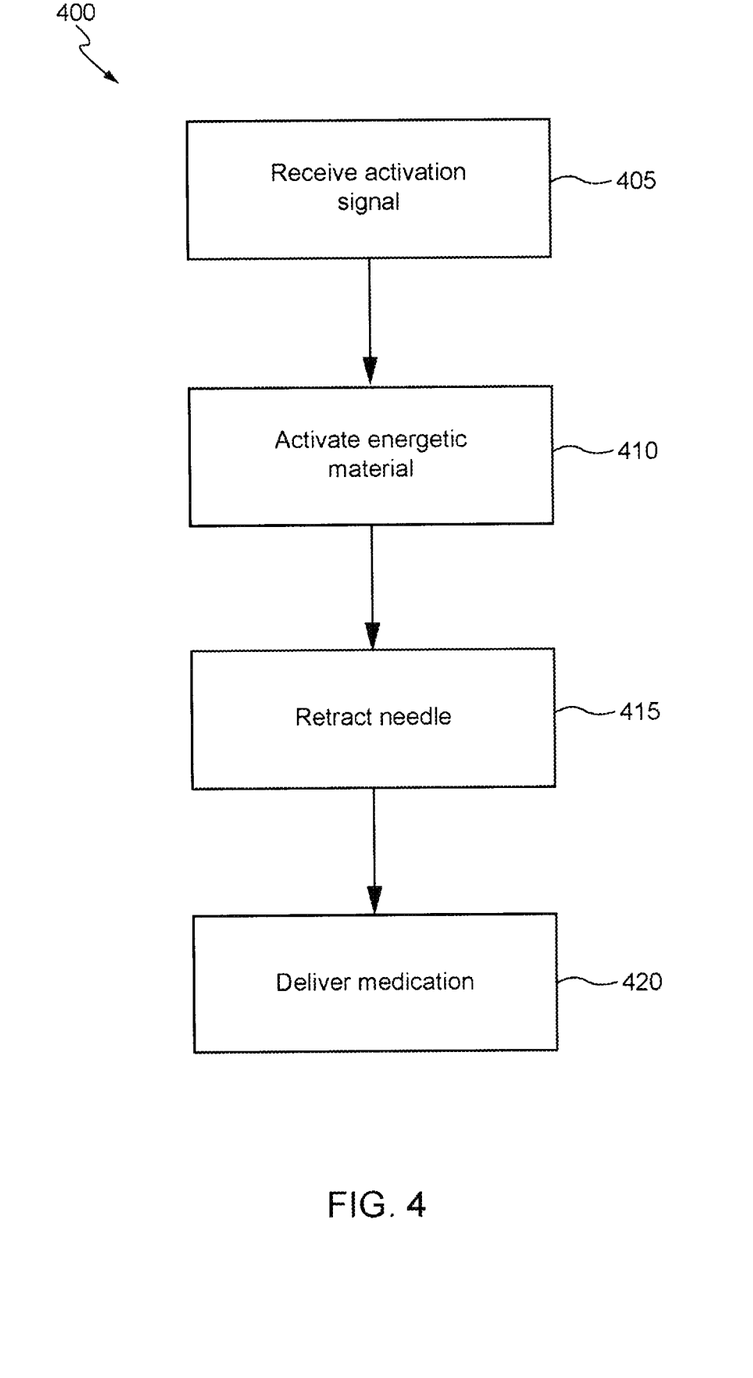
FIG. 4 shows an exemplary flow for delivering an injectable substance to a user with a wearable medical injection device in accordance with various embodiments.

FIG. 4 depicts a simplified flowchart depicting processing performed for delivering an injectable substance to a user according to various embodiments. As noted herein, the flowchart of FIG. 4 illustrates the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions FIG. 4 depicts a simplified flowchart 400 illustrating a process for delivering an injectable substance to a user wearing an injection device. The process will be described with respect to the device 100 shown in FIG. 1 and the system shown in FIG. 2; however, any suitable device or system according to this disclosure may be employed, such as the example devices shown in FIGS. 3A-3K. At step 405, the device 100 receives a command (or commands) to deliver an injectable substance. In this example, the device 100 receives the command from the remote device 210 via a BLE wireless activation signal. To send the command, the remote device 210 may first establish a communications connection with the device 100, such as by pairing with the device using the BLE protocol and then authenticating itself to the device 100, e.g., by providing an encrypted communication comprising a digital signature or certificate. After establishing communications and authenticating itself to the device 100, the remote device 210 transmits an activation signal, which may comprise the command. And while in this example, the remote device 210 authenticates itself to the device 100, such a feature is not required. Instead, the remote device 210 may simply transmit an activation signal, which may comprise the command, such as by broadcasting an activation signal.

At step 410, in response to receiving the command (or commands) to deliver an injectable substance, the device 100 activates the energetic material 155 to generate pressure and force the piston 145 towards an opposite end of chamber. In this example, the firing circuit 175 closes a switch to discharge a capacitor onto an activator in contact with the energetic material 155. The electrical discharge from the capacitor ignites the energetic material 155 and initiates the exothermic reaction. The exothermic reaction generates gasses that fill the chamber 120 and increase the pressure within the chamber 120 behind the piston 145. The pressure eventually surpasses a force of the spring 160, and the piston 145 traverses a portion of the chamber 120 forcing the needle 125 and detachable medication strip 135 through the needle guide 140, optionally the needle cap 130, and the opening 150 of the device 100. If a patient is wearing the device 100, the needle 125 and detachable medication strip 135 are injected into the wearer.

At step 415, the device 100 retracts the needle 125. If a patient is wearing the device 100, a portion of the medication strip 135 remains in the wearer during the retraction of the needle 125. In this example, the spring 160 is compressed by the movement of the piston 145 and pressure generated by the exothermic reaction. After a sufficient amount of the gasses dissipate, e.g., via an exhaust port 167, the spring 160 may ultimately overcome the pressure and retract the needle 125. In additional or alternative embodiments, other needle retraction mechanisms may be employed, such as another propellant charge located beneath the needle cap 130. At step 420, the portion of the strip 135, which remained inside the wearer, delivers the injectable substance to the wearer. For example, the injectable substance may passively elute from the strip 135 into the wearer. Once the injectable substance has been delivered, the wearer may pull off the device 100, and the strip 135 will naturally pull out of the wearer due to the attachment of the strip 135 with the back hub 165 and the attachment of the back hub 165 with the housing 142 via the catch feature 170.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A device for injecting an injectable substance into a user, comprising:
 a housing defining a chamber having a first end and a second end, the second end including an opening of the housing to an external environment;
 a piston disposed towards the first end of the chamber and translatable within the chamber;
 a hollow needle attached to the piston and disposed within the chamber and extending from in a front of the piston towards the second end of the chamber;
 an energetic material disposed within the first end of the chamber and behind the piston to force the piston and the hollow needle towards the second end of the chamber in response to an activation of the energetic material;
 a medication strip disposed within the hollow needle and comprising the injectable substance, wherein the medication strip comprises one or more polymers and the injectable substance is in a non-liquid form that is at least one of: (i) disposed on a surface of the one or more polymers, and (ii) imbibed within the one or more polymers;
 a back hub attached to an end of the medication strip and disposed within the chamber and in the front of the piston;
 a catch feature disposed at the second end of the chamber that includes the opening to the external environment, wherein the catch feature includes a mating structure to: (i) engage and lock the back hub in place at the second end of the chamber once the piston is forced towards the second end of the chamber in response to the activation of the energetic material, such that the engagement and locking of the catch feature with the back hub allows the medication strip to remain in the user upon retraction of the hollow needle; and (ii) inject the hollow needle and the medication strip into the user as the catch feature locks the back hub in place; and
 a spring disposed within the chamber and extending from in front of the piston towards the second end of the chamber, wherein the spring enables the piston and the hollow needle to: (i) retract back towards the first end of the chamber once the piston is forced towards the second end of the chamber in response to activation of the energetic material; and (ii) allow the medication strip to remain in place inside the user as the piston and the hollow needle retract back towards the first end of the chamber.

2. The device of claim 1, further comprising:
a needle guide that defines a curved path that forces the hollow needle to bend towards the opening.

3. The device of claim 1, further comprising a reusable portion comprising: a firing circuit and a receiver, wherein the firing circuit is connectable to the energetic material and configured to activate the energetic material upon receiving an activation command from the receiver.

4. The device of claim 1, wherein the medication strip includes a first portion having a first type of the injectable substance and a second portion having a second type of the injectable substance.

5. The device of claim 1, further comprising an exhaust port that allows dissipation of gas generated in response to the activation of the energetic material.

6. A device for injecting an injectable substance into a user, comprising:
a first portion comprising a firing circuit; and
a second portion connected to the first portion and comprising:
a chamber having a first end and a second end, the second end including an opening of the device to an external environment;
a piston disposed within the chamber;
a needle disposed within the chamber on a first side of the piston;
an energetic material disposed within the chamber on a second side of the piston and connected to the firing circuit;
a medication strip disposed within the needle, wherein the medication strip comprises the injectable substance in a non-liquid form, and wherein the medication strip further comprises one or more polymers and the injectable substance is at least one of: (i) disposed on a surface of the one or more polymers, and (ii) imbibed within the one or more polymers;
a back hub attached to an end of the medication strip and disposed within the chamber on the first side of the piston;
a catch feature disposed within the chamber on the second end that includes the opening to the external environment, wherein the catch feature includes a mating structure to: (i) engage and lock the back hub in place once the piston is forced to traverse the chamber in response to n activation of the energetic material, such that the engagement and locking of the catch feature with the back hub allows the medication strip to remain in the user upon retraction of the needle; and (ii) inject the needle and the medication strip into the user as the catch feature locks the back hub in place; and
a spring disposed within the chamber and extending from the first side of the piston towards the second end of the chamber, wherein the spring enables the piston and the needle to: (i) retract back towards the first end of the chamber once the piston is forced towards the second end of the chamber in response to the activation of the energetic material; and (ii) allow the medication strip to remain in place inside the user as the piston and the needle retract back towards the first end of the chamber.

7. The device of claim 6, wherein the first portion further comprises a battery and one or more capacitors, the battery is configured to store a charge in the one or more capacitors, and the firing circuit is configured to: (i) activate the energetic material by coupling the one or more capacitors to an activator in contact with the energetic material, and (ii) release the stored charge and initiate an exothermic reaction of the energetic material.

8. The device of claim 6, wherein the injectable substance comprises epinephrine or glucagon.

9. The device of claim 6, further comprising:
a needle guide that defines a curved path that forces the needle to bend towards the opening, wherein the needle comprises a hollow tube having one pointed end with an opening.

10. The device of claim 6, wherein the medication strip includes a first portion having a first type of the injectable substance and a second portion having a second type of the injectable substance.

11. The device of claim 6, further comprising an exhaust port that allows dissipation of gas generated in response to the activation of the energetic material.

* * * * *